United States Patent [19]

Litzkow et al.

[11] Patent Number: 4,937,555

[45] Date of Patent: Jun. 26, 1990

[54] PIEZOELECTRIC APPARATUS AND PROCESS FOR DETECTION OF INSECT INFESTATION IN AN AGRICULTURAL COMMODITY

[75] Inventors: Carl A. Litzkow, Newberry; J. C. Webb, Gainesville; Kenneth W. Vick, Newberry, all of Fla.

[73] Assignee: The United States of America as represented by the Secretary of Agriculture, Washington, D.C.

[21] Appl. No.: 332,901
[22] Filed: Apr. 4, 1989
[51] Int. Cl.$^5$ .............................................. G08B 21/00
[52] U.S. Cl. ...................................... 340/540; 73/587; 340/573; 367/180
[58] Field of Search ........................ 340/573, 540, 566; 73/587, 661, 658, 649; 43/132.1; 367/180; 181/125; 310/348, 311

[56] References Cited

U.S. PATENT DOCUMENTS

| | | | |
|---|---|---|---|
| 3,336,573 | 8/1967 | Gallaway et al. | 340/7 |
| 3,494,329 | 2/1970 | Frieberger et al. | 73/584 X |
| 3,792,204 | 2/1974 | Murayama et al. | 310/340 |
| 3,969,927 | 7/1976 | Yoshida et al. | 73/658 |
| 4,028,688 | 6/1977 | Goleman | 340/539 |
| 4,309,576 | 1/1982 | Corrigan | 381/161 |
| 4,415,979 | 11/1983 | Hernandez | 364/508 |
| 4,535,205 | 8/1985 | Ravinet et al. | 381/114 |
| 4,583,405 | 4/1986 | Simmons | 73/584 |
| 4,671,114 | 6/1987 | Litzkow et al. | 73/587 |
| 4,809,554 | 3/1989 | Shade et al. | 73/587 |

FOREIGN PATENT DOCUMENTS 2517833  10/1983  France .

OTHER PUBLICATIONS

K. M. Reese, "ARS People Listen to Insects Inside Fruit", Chemical and Engineering News, Jul. 8, 1985, p. 56.
Pyrah, David, "New System Hears Insects Chewing", Agricultural Research, Apr., 1985, pp. 13-15.
Gourevitch, David, "Researches 'Listen' for Flies Inside Fruit", Gainesville Sun, Sunday, Jun. 9, 1985.
New York Times, Jul. 1985, Science Watch, "Listening to Larvae Chew".
The Atlanta Journal, Tuesday, Aug. 13, 1985, "Fruit Flies Chomp Away While Scientists Listen In".
The Phoenix Gazette, Wednesday, Jul. 24, 1985.
Discover Magazine, Aug. 1985, p. 10, "Maggots Unmasked".
Popular Science, Nov. 1985, Science Newsfront by Arthur Fisher, "Fruitful Listening".
West, Dick, "The Lighter Side", Tuesday, Jul. 2, 1985.
"Amplifier Spots Termites", Popular Mechanics, Nov., 1955, p. 97.
Webb, J. C. et al., "Detecting Insect Larvae in Fruit by Vibrations Produced", J. Environ. Sci. Health, A19(3), 367-375, (1984).
Hagstrum, D. W. et al., "Acoustical Detection and Estimation of Rhyzopertha Dominica (F.) Larval Populations In Stored Wheat", Florida Entomologist, vol. 71, No. 4, Dec. 1988.
Webb, J. C. et al., "A Computerized Acoustical Larval Detection System", Applied Eng. in Agr., vol. 4 (3): 9/88, pp. 268–274.
Vick, K. W. et al., "Sound Detection of Stored–Product Insects that Feed Inside Kernels of Grain", J. Ec. Ent. 81:1489–1493, 1988.
Webb, J. C. et al., "Acoustical System to Detect Larvae in Infested Commodities", Fla. Ent. 71(4), Dec. 1988, pp. 492–504.
BNF Enterprises Peabody Mass., Catalog No. 85P1, 1985, 4 pages.

Primary Examiner—Glen R. Swann, III
Attorney, Agent, or Firm—David R. Sadowski; M. Howard Silverstein

[57] ABSTRACT

Detection of insect infestation in an agricultural commodity is provided by piezoelectric means for generating electricity in response to vibration only of a frequency above about 500 Hertz, in vibrational communication with the agricultural commodity. The present invention may be utilized to detect infestation by a variety of different insects such as rice weevil, lesser grain borer, angoumais moth, in numerous types of agricultural commodities including corn, wheat, rice nuts, cotton, etc.. Various embodiments are disclosed including use of the piezoelectric means, on a probe, with a sample cup, in a device for telemetry, and with various container means for containing an agricultural commodity including e.g. a truck, ship, railroad car and storage bin such as a silo or grain elevator.

23 Claims, 9 Drawing Sheets

ABOUT 4,937,555

PIEZOELECTRIC APPARATUS AND PROCESS FOR DETECTION OF INSECT INFESTATION IN AN AGRICULTURAL COMMODITY

BACKGROUND OF THE INVENTION

1. Field of the Invention

This invention relates to apparatus and processes for non-destructive, non-acoustical and inexpensive detection of insect infestation in agricultural commodities.

2. Description of Prior Art

In this country alone, hidden insect infestation in stored agricultural commodities such as corn, wheat, rice, nuts, cotton, etc., costs the government and farmers millions of dollars each year. This figure is obviously larger when considered on a worldwide basis. Quick, inexpensive, and reliable tools for determining insect infestation are needed, and could prove very beneficial in: (1) determining if a stored commodity is marketable; (2) maintaining good quality of agricultural commodities, and; (3) facilitating enforcement of government food quality regulations.

Various detection methods used in the past included X-ray, chemical or visual analysis, and more recently, acoustical amplification of insect sounds as exemplified by U.S. Pat. No. 4,671,114 issued 6/9/87 to Litzkow et al. All of these methods are expensive, require elaborate testing facilities with trained personnel, and have various drawbacks. For example, X-ray inspection suffers from the drawbacks of: (1) high initial cost for equipment; (2) high cost of X-ray film and development, and; (3) examination of each of the individual grains on the X-ray film requires a great deal of labor. Acoustic detection such as that disclosed by the aforementioned U.S. Pat. No. 4,671,114 suffers from the drawbacks of: (1) requiring extensive acoustical detection elements, such as, at least one sound detecting diaphragm, a backstop, a sound waveguide means, a support member, and a microphone, none of which are necessary for the present invention; (2) being susceptible to interference from extraneous sound thus requiring operation thereof in a sound dampened environment, in contrast to the present invention which provides similar sensitivity but surprisingly is not as susceptible to such interference.

The Federal Grain Inspection Service has no limits on larval infestation because until now there have been no devices to test for larvae. At present, grain is inspected visually by sieving the grain through hardware cloth and filtering out the adult insects. Active larvae inside the grain cannot be seen, which may result in a failure to detect such larvae. Our invention permits detection of both adult insects and hidden larvae.

SUMMARY

The present invention avoids the problems of the prior art, and provides novel and highly unobvious detection of insect infestation i.e. insects at all stages of maturity including larvae (such as e.g. rice weevil, lesser grain borer, angoumais moth, etc.) in an agricultural commodity such as corn, wheat, rice, nuts, or cotton.

The apparatuses of the present invention comprise:

container means for holding an agricultural commodity, the container means defining therein an interior, and;

a piezoelectric means for generating electricity in response to vibration only of a frequency above about 500 hz, the piezoelectric means being exposed to the interior of the container means, so that when an agricultural commodity is placed in the container the piezoelectric means will be in vibrational communication with the agricultural commodity.

The processes of the present invention comprise:

placing a piezoelectric means for generating electricity in response to vibration only of a frequency above about 500 hertz in vibrational communication with an agricultural commodity, and;

determining if said piezoelectric means generates electricity as a result of vibration produced by at least one insect infesting the agricultural commodity.

Advantages of the instant invention over acoustic systems such as that disclosed in the aforementioned U.S. Pat. No. 4,671,114 include: eliminating the need for at least one sound detecting diaphragm, a backstop, a sound waveguide means, a support member, and a microphone; thus providing less expensive, more reliable durable, compact, lightweight, portable and more readily waterproofable devices which are not susceptible to influence from extraneous sounds, and which may readily be operated by a person having only minimal training and no technical background.

DESCRIPTION OF THE PREFERRED EMBODIMENTS

Figure 1:
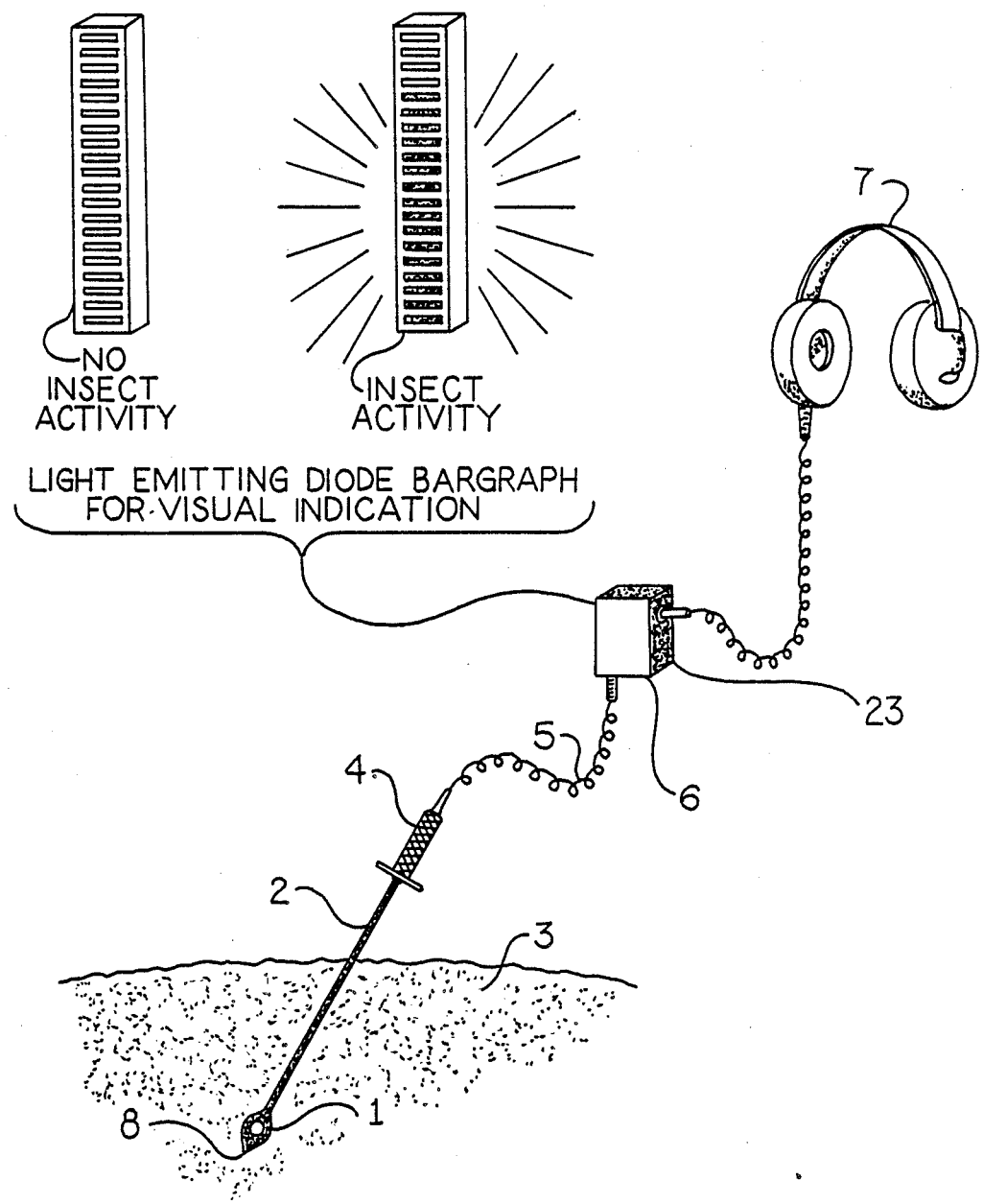
FIG. 1 is a schematic representation of a first embodiment of the present invention which includes a probe.

A first aspect of the present invention relates to a probe, as exemplified by that shown in FIG. 1. Said probe includes a shaft designated 2, having a piezoelectric element (means) for example a disc or film, such as a piezoelectric layer deposited on support such as brass, ceramic, glass, a plastic film such as MYLAR ™ etc., designated 1, mounted adjacent a first end of said shaft 2, and a handle or grip designated 4 attached to said shaft adjacent a second end thereof. Said piezoelectric element may be any of a variety of commercially available piezoelectric elements; for example, devices commercially available for use as output devices (rather than input devices) such as a piezoelectric ceramic buzzer found in burgler alarms, automotive warning devices, and electronic games. Such elements generate electricity in response to vibration only of a frequency above about 500 hertz. It is necessary that the piezoelectric means generates electricity only in response to vibration above about 500 hertz because troublesome low frequencies are never produced, therefore low frequency filtering is virually eliminated. This allows use of a much simpler and inexpensive amplifier. In use an inspector may grasp the handle/grip 4 and push at least a portion of the probe into the agricultural commodity 3 (e.g. corn, wheat, rice, nuts, cotton) which is to be tested for insect infestation. While for many uses the shaft 2 may be about one meter in length, it may in fact be made of any convenient length depending e.g. on how far the piezo disc is to be inserted into the agricultural commodity 3, or the shaft may be extendable or configured to accept extensions so as to provide greater length. A shielded cable designated 5 extends from the piezo element 1 to a combination electronic amplifier and filter designated 6. Such a combination filter and amplifier is well known in the electronics art, and may for example be an inexpensive battery powered high gain preamplifier/amplifier combination sold by Radio Shack designated by part numbers 277-10088 and 32-2031A. Such electronics are typically small enough to be housed in a container roughly the size of a cigarette pack, or may more conveniently be incorporated either into shaft 2 or the headphones 7. The combination electronic amplifier and filter 6 functions to, receive relatively low-voltage electrical signals generated by the piezo element 1 and, produce a signal which provides a readily audible sound from headphones 7. Such a probe has the advantages of: inexpensiveness, providing an excellent signal-to-noise ratio, and being quick and easy to operate (e.g. the probe may be inserted at various positions to varying depths to monitor for insect activity without actually having to remove any sample(s) for visual inspection, thus: (1) saving time over a visual inspection; (2) allowing detection in a volume of commodity which far exceeds the volume an inspector could visually inspect in the same length of time, and; (3) permitting detection of larvae that are inside the agricultural commodity (i.e. not visible and thus could not be detected by visual inspection). Another unobvious and significant advantage of the probe is that when the probe tip is inserted into an agricultural commodity even only to a depth of a few centimeters, the surrounding commodity provides shielding from vibrations originating outside the commodity. Thus, extraneous vibrations e.g. from the operation of heavy assembly and loading equipment only a few meters away from the probe does not interfere with its detection of insects.

Figure 2:
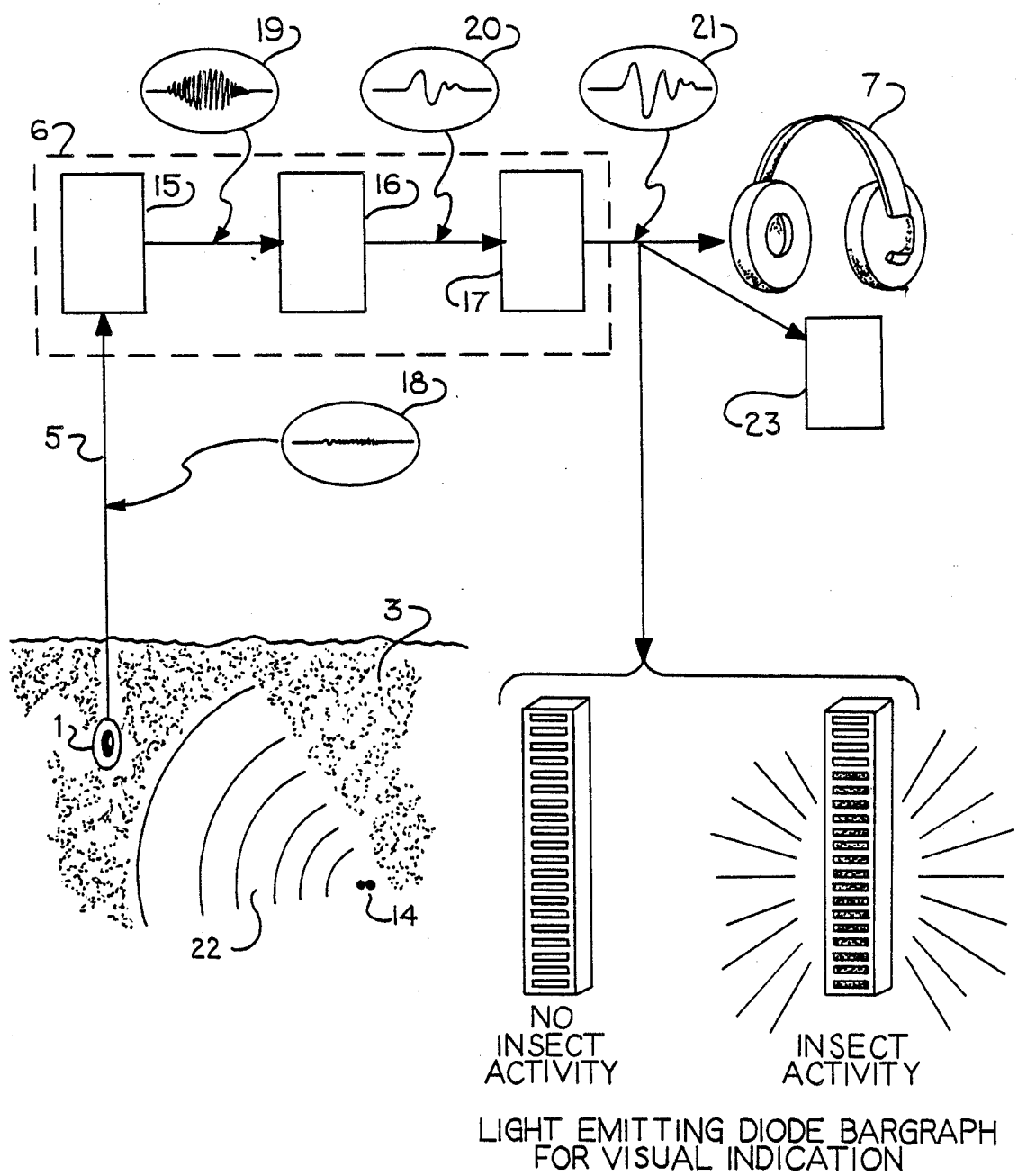
FIG. 2 is a block diagram showing in greater detail the basic electronic components of an embodiment of the present invention.

FIG. 2 is a simplified block diagram of basic electronic components which may be utilized in a detection device of the present invention. Vibrations designated 22 produced by chewing or moving of an insect (the term "insect" is used herein to encompass insects at all stages of maturity including larva) designated 14 are transmitted through commodity 3 and act upon the piezo element 1 to produce relatively weak low-level electrical signals 18. These weak signals are electrically transmitted through shielded cable 5 to the preamplifier means 15 (e.g. a Radio Shack model number 277-10088 which is the input stage for the combination amplifier-filter 6 (the components of which are shown in FIG. 2 in a dashed rectangle). A bandpass filter means 16 may be provided. Bandpass filtering may be as simple as a 0.01 microfarad coupling capacitor which takes the preamplified signal 19 and filters out those frequencies above and below the desired biologically generated frequencies to assist the inspector in discriminating insect activity from various non-biological background noises. The filtered signal 20 then goes to the input of the driver amplifier means 17, (which may for example be a model 33-2031A from Radio Shack) which amplifies this preconditioned signal to a signal of sufficient level 21 to drive a pair of headphones 7. The devices of either FIG. 1 or FIG. 2 may use in addition to or in place of the headphones 7 other indicator means such as a gauge, meter, dial or display (e.g. a 20-segment red-light-emitting diode array available from National Semiconductor, Santa Clara, California, incorporated into the device using two IM-3914 integrated circuits available from Radio Shack, Mouser, Digi-key and other electronic suppliers). Use of such a display(s) when used in combination with the headphones gives a visual reinforcement to the audio signals produced by insect activity. Also, the devices of either FIG. 1 or 2 may include a radio transmitted designated 23 used in addition to or in place of the headphones or other indicator means. Said radio transmitter may for example be a small inexpensive FM wireless microphone modified to accept the output from the amplifier-filter 6 rather than the input from the original microphone, as for example a model #WM002T from RCA. The radio transmitter functions to transmit data to a remote receiving station. Use of such a transmitter and receiver: allows convenient remote monitoring; permits the signals from a plurality of such detection devices to be monitored at a single location, and facilitates making permanent records of insect activity, especially when the detection device(s) is/are in a location (such as on top of a tall grain elevator or silo) where transporting and/or operating recording devices such as magnetic tape recorders or paper tape strip chart recorders would be awkward or hazardous.

Figure 3:
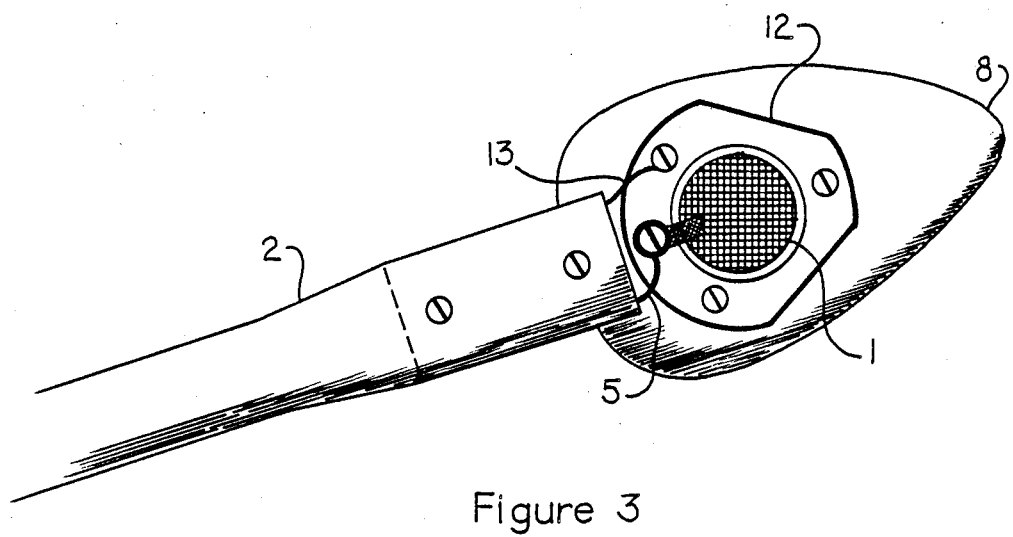
FIG. 3 shows detail of the tip of the probe of FIG. 1.

FIG. 3 illustrates an example of construction details of a probe-tip for a probe of the type shown in FIG. 1. A shaft 2 constructed from a 19 mm diameter electrical conduit is shown slightly flattened and drilled to accept two 4-40 machine screws which secure a 3/8-inch thick PLEXIGLASS TM tip designated 8. The tip 8 may be rounded on all edges to make insertion and removal from an agricultural commodity 3 easier. The active element on the piezo disc 1 is electrically connected to the preamplifier 15 (FIG. 2) via shielded cable 5. The ground wire 13 is electrically continuous from signal ground in the combination amplifier-filter 6 (FIGS. 1 and 2) to the piezoelectric disc substrate 12 (which may for example be brass) of the piezo disc 1. The electrical conduit pipe shaft 2 is also at signal ground potential to minimize R. F. pick-up or antenna effect. Three 4-40 machine screws mechanically secure the piezo disc 1 and substrate 12 to the PLEXIGLASS TM tip 8.

Figure 4:
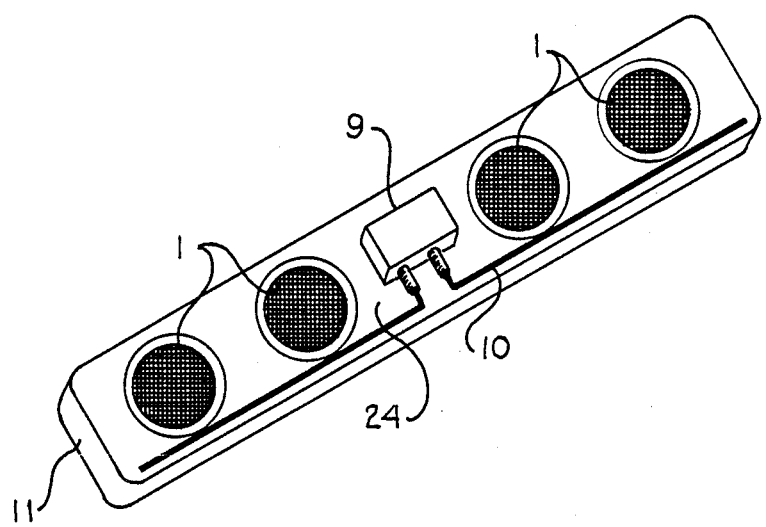
FIG. 4 illustrates a second embodiment of the instant invention, which is a device for telemetry of data.

FIG. 4 illustrates a second embodiment of the present invention, relating to devices suitable for telemetering data to a receiver. More specifically, the device for telemetry designated generally by numeral 24 shown in FIG. 4 includes four piezo discs (i.e. elements) designated 1 (although it should be understood that any number of such discs/elements may be employed) mounted on any suitable non-conductive base 11 (such as a PLEXIGLAS TM or LEXAN TM strip), each said disc being connected to a frequency modulated transmitter and amplifier (FMTA) designated 9 (which may for example be a RCA transmitter model #WM002T and a Radio Shack amplifier 32-2031A). Said FMTA 9 transmits a radio signal through the transmitter antenna 10 to a suitable receiver (not shown) such as the receiver provided with the RCA model #WM002T.

Figure 5:
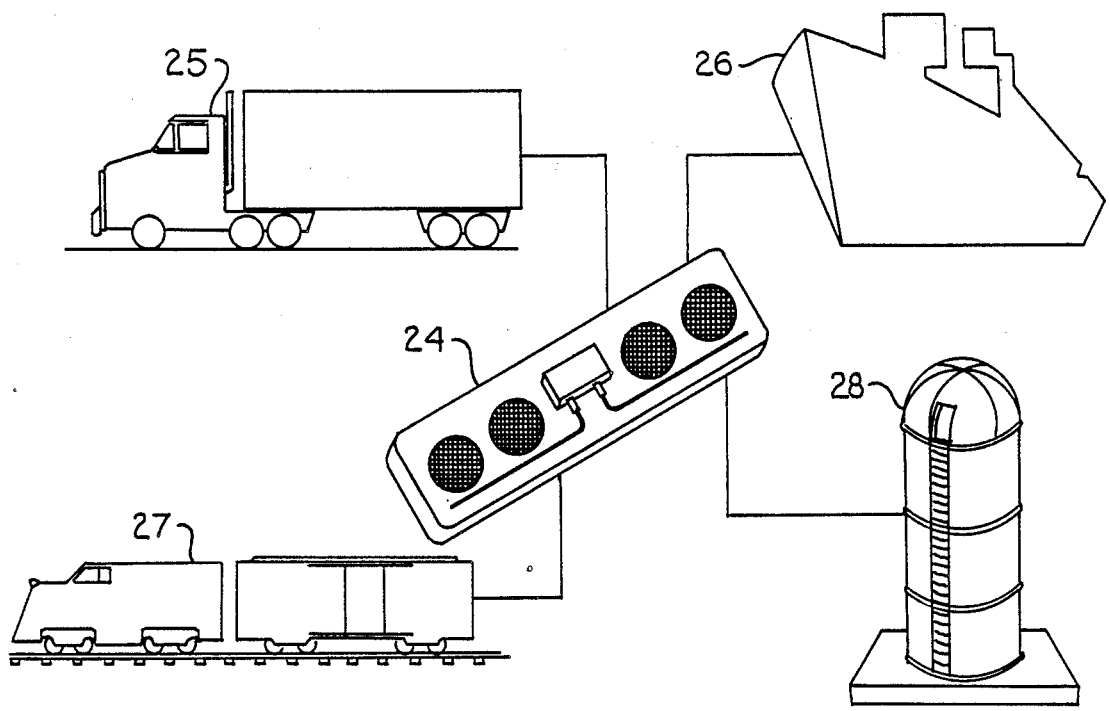
FIG. 5 illustrates examples of application for telemetry for devices of the present invention.

FIG. 5 illustrates schematically a variety of container means for holding an agricultural commodity with which the device for telemetry 24 of FIG. 4 may be utilized. As shown in FIG. 5, said container means may for example take the form of: (1) land transport such as a truck 25; (2) ship transport, which includes for example a ship designated 26 i.e. a boat, barge, etc.; (3) rail transport in a railroad car 27 i.e. a box car or other railroad car configured for agricultural commodity transport, or; (4) storage bin 28 including a silo, grain elevator, etc. The device for telemetry may be incorporated into said container means by: (A) simply throwing one or more devices into the agricultural commodity as it is loaded into the container means;, (B) burrying and/or inserting one or more devices into the agricultural commodity after the agricultural commodity has been deposited into the container means; (C) disposing one or more devices into a side wall and/or bottom of the container means; and/or (D) disposing one or more devices each of which is positioned on an arm within the container means.

Figure 6:
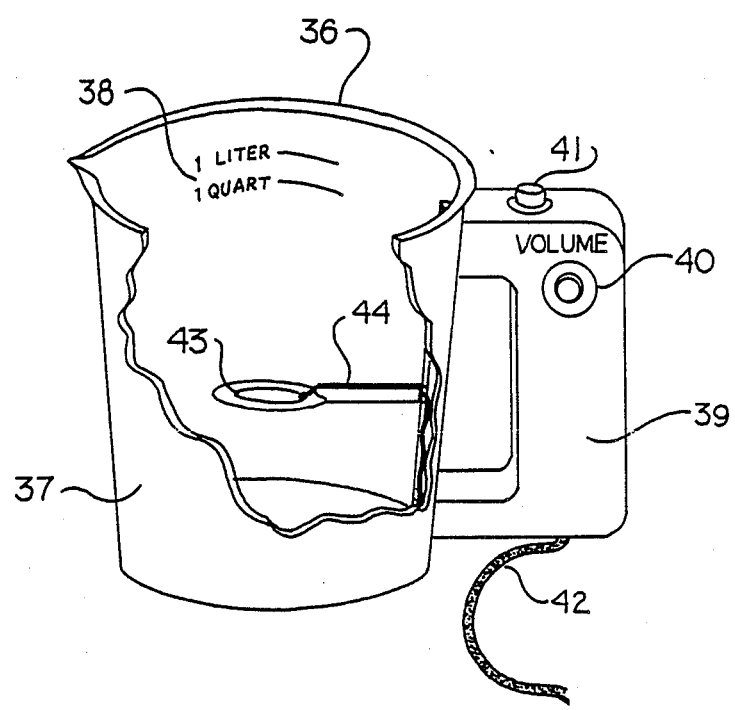
FIG. 6 illustrates a third embodiment of the present invention, which is a sampling and testing container e.g. cup or scoop.

FIG. 6 illustrates a third embodiment of the present invention, which is a hand held sampling device (which may be termed a cup or scoop), generally designated by numeral 36. Said device may include, a container means 37, which may for example define therein an interior volume of slightly more than 1 liter. The container means 37 may be provided with indicia 38 thereon indicating the volume of agricultural commodity held within the container means. Optionally, a handle 39 may be mounted in the container means to facilitate manipulation of said container means. In the embodiment shown in FIG. 6 the electronics (e.g. amplifier, volume adjustment means 40, on/off switch 41, etc.) are, for convenience, incorporated into the handle 39, although it should be understood that said electronics may instead, be incorporated into a separate container as shown in FIG. 1 or, be incorporated into headphones. FIG. 6 also shows a wire 42 connecting said electronics to headphones not shown. The container means has exposed to the interior thereof a piezoelectric means (e.g. a piezoelectric disc 43) connected to said electronics. Although, FIG. 6 shows for purposes of illustration only a piezo disc held approximately at the center of said container means by an arm 44, the present invention also encompasses other configurations in which an agricultural commodity placed within the container means is in vibrational communication with piezoelectric means. Examples of such configurations include: (1) disposing one or more piezoelectric element(s) in or on the sidewall or bottom of the container, or; (2) utilizing two or more piezo elements, each held by an arm at various points in the interior of the container means, thereby providing close proximity between at least one piezo element and all portions of the agricultural commodity. In use of the device of FIG. 6, the agricultural commodity is placed within the interior of the container means, as for example by grasping the handle and dipping the container means into a large quantity of the commodity in a manner to fill or substantially fill said container means. The electronics are then activated by depressing the on/off switch 41. If the agricultural commodity is infested, a readily audible sound will be provided by the headphones. This sound may be adjusted to a comfortable level by adjustment of the volume adjustment means 40.

Any of the aforementioned devices of the present invention may employ a variety of power sources including, battery and/or A. C. power. When battery power is utilized it may be desirable to utilize conventional means for indicating low battery voltage, such as the commercially available ICM 7201 Low Battery Voltage Indicator available from Intersil, Cupertino, California. This device lights a red warning light when the battery voltage is low, i.e. the battery needs replacement or recharging.

EXAMPLE 1

The purpose of this example is to illustrate construction of a probe and electronics of the type illustrated in FIGS. 1–3, and to show that results using such a probe are comparable to results achieved using a less convenient method of detection (requiring that grain samples be taken and acoustically evaluated) as described by Vick et al "Sound-detection of Stored-product insects that feed inside kernels of grain", J. Econ. Entomol. 81:1489–1493, 1988. A probe was constructed using: a durable piezoelectric disc #DO576 from BNF Enterprises, Peabody, Mass. mounted on the end of a shaft; a battery operated Insecta-Scope amplifier from Sound Technologies Inc. Kigore, TX, and; earphones. A Krohn-Hite model 3700 filter was connected between the amplifier and the earphones to filter out frequencies below 100 hz and above 3000 hz. Output was recorded on a Technics Magnetic tape recorder Model RS-B16 equipped with dBX. Magnetic tape recordings of data were analyzed with a Fast Fourier Transformation (FFT) instrument (Nicolet Model 660A) and a Hewlett Packard Vectra computer to compare earphone with instrument counts. The FFT determined the frequency content, whereas instrument counts with the Hewlett Packard Vectra computer coupled through a Hewlett Packard universal counter Model 5316A determined the number of voltage spikes in a predetermined time interval (Webb et al 1988, "A Computerized acoustical larval detection system", Applied Eng. in Agriculture, 4:268–274). The probe was tested for detection of lesser grain borer Rhyzopertha dominica (F.) larva in wheat.

Figure 7:
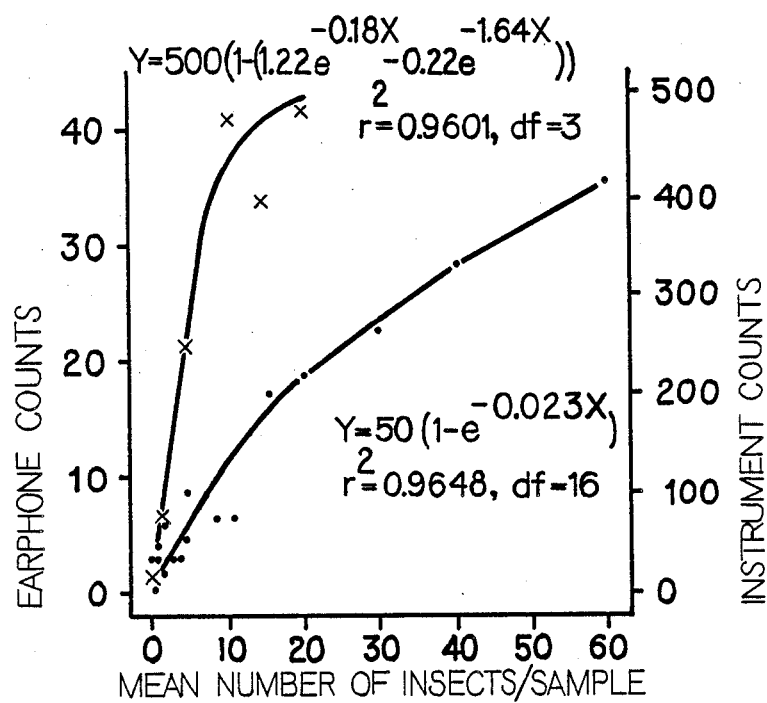
FIG. 7 is a graph of earphone and instrument counts vs. mean number of insects per sample for the detection method of Vick et al and the detection method of the present invention.

Insect population of several densities were prepared by diluting lesser grain borer cultures with clean wheat. The actual densities and age structure of the lesser grain borer populations were determined at each density level by x-raying 90 ml samples of wheat. The probe of the present invention was used: (1) to estimate insect densities by counting the number of vibrations per unit of time produced by insects at each of nine locations during a one minute interval in a grain mass (10 cm deep by 14 cm diameter) in a four-liter jar, or; (2) to determine the probability of detection from the fraction of nine locations in a grain mass (10 cm deep by 30 cm diameter) in a 20-liter can at which sounds were heard during 20-s intervals. Both containers were set on 10 cm thick synthetic foam inside a 40 cm diameter cylinder of 5 cm thick synthetic foam to dampen background sound. The probe of the present invention was inserted 3 cm deep in the grain at the centers and at eight equidistant locations halfway between the centers and edges of the containers. A series of 1:1 dilutions was repeated four times in each size of container. The results are shown in FIG. 7 which is a graph of counts vs. mean number of insects per sample, for both the aforementioned method of Vick et al (represented by X's) and the probe of the present invention (represented by dots). As shown in FIG. 7 the number of counts detected with the piezoelectric probe pushed into the grain increased as the density of lesser grain borer larvae increased. This is consistent with the results of the aforementioned Vick et al 1988 article for an acoustical system which required that grain samples be taken. With either method the relationship between the number of sounds or voltage spikes counted and the number of lesser grain borer larvae present was not linear. The nonlinear increase is probably the result of an increased simultaneous occurrence of sounds or vibrations of insects which cannot be separately distinguished.

This example shows that the probe of the present invention provides for rapid and readily accomplished detection and estimating of insect populations in an agricultural commodity and acceptable probability of detection and accuracy of estimation.

EXAMPLE 2

Figure 8:
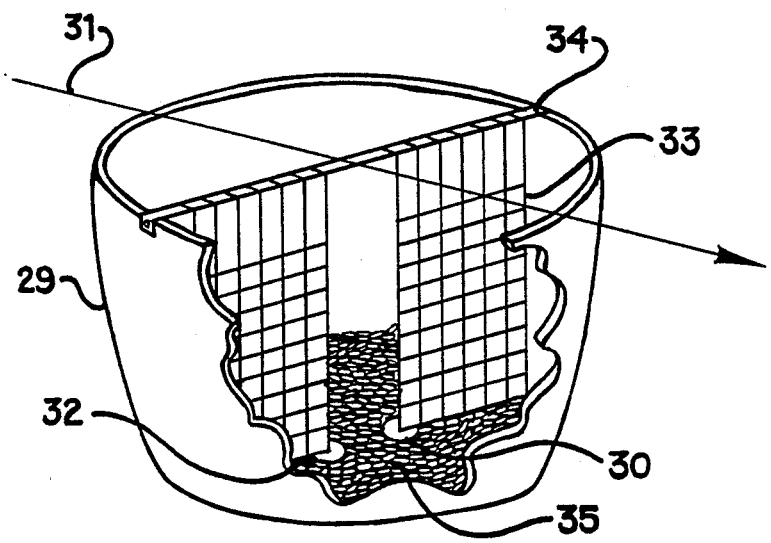
FIG. 8 shows a device as described in example 2, for measuring infestation detection by a piezo disk of the present invention as compared with detection by an acoustic coupler.
Figure 9:
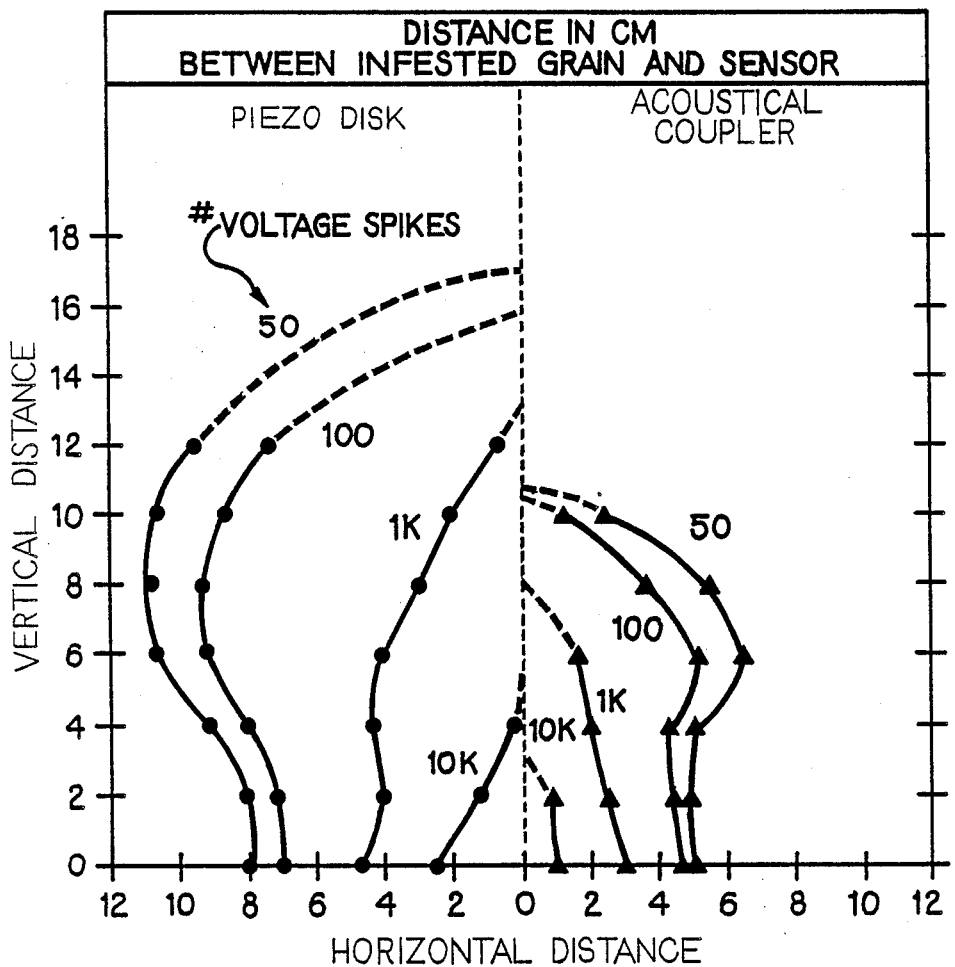
FIG. 9 is a graph showing results achieved with the device shown in FIG. 8 and as described in example 2.

The purpose of this example is to show the improved results achieved by use of the present invention as compared to results achieved with an acoustic coupler. A device as shown in FIG. 8 was constructed including: a container 29 having in the base thereof both an acoustic coupler 30 of the type disclosed in U.S. Pat. No. 4,671,114 (a Bruel and Kjaer model 4145 microphone) and a piezo disc 32 (part #6024 from Jerryco, Inc., Evanston, Indiana) placed equidistant on either side of center line 31. To test the sensitivity of each of these detectors, fifty pounds of unifested grain 35 was placed in the container, and a ½ inch square packet containing five kernels of infested grain was placed at various distances from both detectors. In order to facilitate measurement of the distances from the packet to the piezo disc and acoustic coupler, a grid 33 having 2 cm by 2 cm squares marked thereon was hung from a bar 34 into the interior of the container. A Universal Counter from Hewlett-Packard model 5316A, Palo Alto, California, counted the activity pulses. The results of this comparison are shown in FIG. 9, which is a graph of the number of voltage spikes counted at various distances from the detectors. As may be readily observed from FIG. 9, the device of the present invention produced a similar number of spikes at greater distances than the acoustical coupler device i.e. is clearly able to detect infestation at greater distances than the acoustical coupler. Clearly said graph shows the surprising result that the device of this example may reliably detect only five infested grains from distances of 15 centimeters and more. Another advantage of the instant invention illustrated by this example, is that while the piezoelectric disc only costs $0.75 the Bruel and Kjaer microphone costs $1300, thus providing greatly improved results at only about 1/1733 the cost.

INDEX OF APPARATUS ELEMENTS DESIGNATED BY A NUMERAL

| | |
|---|---|
| 1. piezoelectric element | 21. amplified signal |
| 2. shaft | 22. vibrations |
| 3. agricultural commodity | 23. radio transmitter |
| 4. handle or grip | 24. device for telemetry |
| 5. shielded cable | 25. truck |
| 6. electronic filter and amplifier | 26. ship |
| | 27. railroad car |
| 7. headphones | 28. storage bin |
| 8. tip | 29. container |
| 9. frequency modulated transmitter and amplifier | 30. acoustic coupler |
| | 31. center line |
| 10. transmitter antenna | 32. piezo line |
| 11. base | 33. grid |
| 12. piezoelectric disc | 34. bar |
| 13. ground wire | 35. grain |
| 14. insect | 36. sampling device |
| 15. preamplifier | 37. container means |
| 16. bandpass filter means | 38. indicia |
| 17. driver amplifier means | 39. handle |
| 18. low-level electrical signals | 40. volume adjustment means |
| 19. preamplified signal | 41. on/off switch |
| 20. filtered signal | 42. wire |
| | 43. piezoelectric disc |
| | 44. arm |

We claim:

1. A process for detecting insect infestation in an agricultural commodity comprising:
   placing a piezoelectric means for generating electricity in response to vibration only of a frequency above about 500 Hertz in vibrational communication with an agricultural commodity, and;
   determining if said piezoelectric means generates electricity.

2. The process of claim 1 wherein said agricultural commodity is selected from the group consisting of corn, wheat, rice, nuts or cotton.

3. The process of claim 1 further including the steps of filtering and amplifying the electricity generated by said piezoelectric means.

4. The process of claim 1 further including a step of telemetering including transmitting a radio signal indicative of electricity generated by said piezoelectric means to a radio receiver means.

5. The process of claim 1 wherein said step of determining includes indicating said electricity generation with an audio or visual indicator means.

6. The process of claim 1 wherein said step of placing includes inserting a probe-mounted piezoelectric means into a quantity of agricultural commodity.

7. The process of claim 1 wherein said piezoelectric means is configured as a disc or sheet.

8. The process of claim 1 wherein said agricultural commodity is contained within container means selected from the group consisting of a truck, ship, railroad car or bin.

9. The process of claim 8 wherein said bin is a silo or grain elevator.

10. The process of claim 1 further including the step of recording generating of electricity by said piezoelectric means.

11. An apparatus for detecting insect infestation in an agricultural commodity comprising:
    container means for containing an agricultural commodity, said container means defining therein an interior, and;
    a piezoelectric means for generating electricity in response to vibration only of a frequency above about 500 Hertz, said piezoelectric means being exposed to said interior of said container means, so that when an agricultural commodity is placed in said container said piezoelectric means will be in vibrational communication with said agricultural commodity.

12. The apparatus of claim 11 wherein said container means contains within said interior thereof an agricultural commodity selected from the group consisting of corn, wheat, rice, nuts or cotton.

13. The apparatus of claim 11 further including means for filtering and amplifying the electricity generated by said piezoelectric means, electrically connected to said piezoelectric means.

14. The apparatus of claim 11 further including radio transmitter means, in electrical communication with said piezoelectric means, for transmitting a radio signal indicative of the electricity generated by said piezoelectric means.

15. The apparatus of claim 14 further including radio receiver means for receiving said radio signal transmitted by said radio transmitter means.

16. The apparatus of claim 11 further including audio or visual indicator means, in electrical communication with said piezoelectric means, for indicating said generating of electricity, by said piezoelectric means.

17. The apparatus of claim 11 wherein said container means defines an interior volume of about 1 liter, and further including a handle mounted on said container means.

18. The apparatus of claim 17 wherein said piezoelectric means is held by an arm within said interior of said container means.

19. The apparatus of claim 11 wherein said piezoelectric means is configured as a disc or sheet.

20. The apparatus of claim 11 wherein said container means is selected from the group consisting of a truck, ship, railroad car or bin.

21. The apparatus of claim 20 wherein said bin is a silo or grain elevator.

22. The apparatus of claim 11 further including recording means, in electrical communication with said piezoelectric means, for recording said generating of electricity by said piezoelectric means.

23. The apparatus of claim 11 wherein said piezoelectric means comprises a thin layer of piezoelectric material on a substrate selected from the group consisting of brass, ceramic, glass or plastic film.

* * * * *